United States Patent [19]

Farmer et al.

[11] Patent Number: 5,141,512
[45] Date of Patent: Aug. 25, 1992

[54] ALIGNMENT OF HIP JOINT SOCKETS IN HIP JOINT REPLACEMENT

[76] Inventors: Malcolm H. Farmer, "Eldorado", Bray Road, Cabinteely, Co. Dublin; James Doyle, 40, The Rise, Boden Park, Dublin 16; Anthony C. Hooper, 42, Fosters Avenue, Mount Merrion, Co. Dublin; Patrick O'Mahony, "Waloma", Ballyvelly, Tralee, Co. Kerry, all of Ireland

[21] Appl. No.: 574,530

[22] Filed: Aug. 28, 1990

[30] Foreign Application Priority Data

Aug. 28, 1989 [IE] Ireland ................... 2761/89

[51] Int. Cl.⁵ .............................................. A61F 2/34
[52] U.S. Cl. ....................................... 606/87; 606/89; 606/91
[58] Field of Search .................. 606/54, 86, 87, 88, 606/89, 90, 91, 99, 102; 623/22, 23

[56] References Cited

U.S. PATENT DOCUMENTS

| | | | |
|---|---|---|---|
| 3,859,992 | 1/1975 | Amstutz | 606/91 |
| 4,305,394 | 12/1981 | Bertuch, Jr. | 606/91 |
| 4,475,509 | 10/1984 | Oh | 606/91 |
| 4,528,980 | 7/1985 | Kenna | 606/102 X |
| 4,716,894 | 1/1988 | Lazzeri et al. | 606/99 X |

FOREIGN PATENT DOCUMENTS

| | | |
|---|---|---|
| 0263292 | 4/1988 | European Pat. Off. |
| 0265659 | 5/1988 | European Pat. Off. |
| 2214815 | 9/1989 | United Kingdom . |

Primary Examiner—Robert A. Hafer
Assistant Examiner—Sam Rimell
Attorney, Agent, or Firm—Young & Thompson

[57] ABSTRACT

An apparatus for aligning an acetabular cup for proper placement in a socket in hip joint replacement includes a frame having feet which are placed against and fastened to the anterior superior iliac spines and the pubic tubercles respectively of the pelvis. A light beam is directed from a source through an aperture to a mirror mounted on an implant inserter. The light beam is reflected back from the mirror to a target region. When the incident and reflected beams are coincident, the cup is aligned for correct placement. The target region is rotatably and pivotably mounted for precise adjustment of the angles of abduction and anteversion respectively.

20 Claims, 6 Drawing Sheets

FIG. 12

ALIGNMENT OF HIP JOINT SOCKETS IN HIP JOINT REPLACEMENT

BACKGROUND OF THE INVENTION

1. Field of the Invention

This invention relates to the positioning of hip sockets into prepared cavities int eh acetabulum of the pelvis in total hip joint replacement. The invention also relates to apparatus for this purpose, to the design and construction of such apparatus, as well as to a method of using the apparatus, and applies to all types of sockets, adhesives, and inserters which may be employed in the method. The invention also relates to apparatus for training surgeons int he placement of acetabular implants in hip joint replacements.

2. Description of the Prior Art

In hip joint replacement, it is common practice to utilise a socket inserting instrument, for example, typically a Charnley socket holder and orientation guide, for holding and introducing a polyethylene socket into the prepared cavity in the acetabulum of the pelvis. This socket holder is constructed to hold the socket on a free end extremity of a rod. A handle is fixed to the rod in the vicinity of its other end. The handle may typically be at right-angles to the longitudinal axis o the rod but other angles may also be used. A suitable adhesive is introduced into the prepared acetabular cavity and on the mating face of the socket, and the socket is then inserted into the cavity, using the socket holder. The surgeon holds the socket holder and manoeuvres it manually to orientate the socket into a disposition which is established by the skill, judgement and experience of the surgeon. In essence, the surgeon uses a visual method in which he tries to align two perpendicular straight bars defining the rod of the Charnley device and its handle, one of the bars being aligned with the longitudinal axis of the body and the other bar being aligned wit the transverse axis through the pelvis. However, since during a hip joint replacement operation, the patient's body is in a twisted position and is also covered with sterile cloths, the carrying out of this known method is not only extremely difficult but is also somewhat haphazard.

As a result therefore, a significant proportion of sockets cemented into cavities in hip joint replacement operations are disposed at an incorrect angle and this may cause the replacement hip joint to become dislocated. Dislocation may occur in particular if the legs are moved excessively far apart, in which circumstances the joint may actually come apart. Such a result causes great problems, not to mention actual pain, for the patient involved. A particular difficulty experienced by a surgeon in optimising the orientation of the socket arises form the absence of any straightforward method of defining a reference plane on the pelvis relative to which the appropriate angle may be set out. In addition the instruments currently available are not equipped with scales or protractors to supplement the visual judgement of the surgeon and his manual dexterity.

BRIEF SUMMARY OF THE INVENTION

It is an object of the invention to provide apparatus which will facilitate improved placement of implants in hip joint replacement. It is a further object of the invention to provide an improved method of placing implants in correctly aligned dispositions in hip joint replacement. A still further object of the invention is the provision of apparatus enabling surgeons to practise and perfect their skill in placing implants in hip joint replacement.

According to a first aspect of the invention, there is provided apparatus for facilitating aligned location of an acetabular implant in hip joint replacement, comprising frame means for locational juxtaposition adjacent to selected pelvic features of a patient to define a reference plane, means for positioning an acetabular implant in the hip socket, said implant positioning means having an implant mounting portion, and means for determining the disposition of said implant positioning means with respect to said reference plane so that the disposition of an implant mounted on said positioning means relative to said reference plane may be monitored and controlled.

Preferably the frame means has wing portions for juxtaposition adjacent to the anterior superior iliac spines of the pelvis and a further portion or portions for juxtaposition against the pubic tubercles of the pelvis. The apparatus may also incorporate means for affixing said frame means to said features of the pelvis.

Said disposition determining means may include means for emitting a directed beam and target means towards which said beam is directable, correct alignment of the implant positioning means being indicated by impact of the beam on a specified region of the target means. Alternatively detection means such as a plurality of sensors co-operating to provide an output signal on a display device may substitute for the target means. In an especially preferred embodiment, the disposition determining means includes a reflector such as a mirror mountable on the implant positioning means to reflect said directed beam towards said target means.

In said configuration, the disposition determining means may comprise a light source mounted on the frame means for reflection of said beam back along its initial path when the implant positioning means is correctly aligned. The light source may be a laser source. The apparatus is suitably formed from materials capable of sterilisation without deterioration, or it may be at least partially a disposable unit, the frame for example being discarded after use.

In a further aspect of the invention there is provided apparatus for facilitating aligned location of an acetabular implant in hip joint replacement comprising frame means for locational juxtaposition adjacent to selected pelvic features of a patient to define a reference plane, and means for determining the disposition of an implant positioning means with respect to said reference plane so that the disposition of an implant received on a mounting portion of said implant positioning means relative to said reference plane may be monitored and controlled.

According to an especially preferred embodiment of the present invention, there is provided apparatus for facilitating aligned location of an acetabular implant in hip joint replacement comprising frame means for locational juxtaposition adjacent to selected pelvic features of a patient to define a reference plane, and means for determining the disposition of an implant positioning means with respect to said reference plane so that the disposition of an implant received on a mounting portion of said implant positioning means relative to said reference plane may be monitored and controlled, wherein the frame means comprises two foot portions for juxtaposition adjacent tot he anterior superior iliac spines of the pelvis and at least one further foot portion for juxtaposition adjacent to one or both pubic tubercles of the pelvis, a central frame region from which limbs extend to said foot portions, and a light-source mounting portion which is pivotably displaceable relative to said central region of the frame about at least one axis.

The frame is preferably dimensioned so that when said foot portions are juxtaposed against said iliac spines and pubic tubercles, said at least one axis extends substantially perpendicular to a coronal plane defined by these anatomical reference points. The light-source mounting frame portion may have means for receiving a source of collimated light for direction towards a reflector mounted on said implant positioning means, said reflector defining a further portion of the disposition determining means of the apparatus of the invention. The spacing of said foot portions from said central region of the frame may be adjustable to enable use of the apparatus of the invention on a variety of different sizes of patient and under a diversity of operating conditions. The orientation of the foot portions may also be variable relative to the central region of the frame.

The light-source mounting means may comprise a turntable portion which is rotatable relative to said central frame region about said axis generally perpendicular to he coronal plane defined by the anatomical features previously adverted to and engaged by the foot portions in use of the invention. The light-source may be arranged for direction of a light beam substantially at right angles to said perpendicular axis, i.e. generally parallel to the coronal plane in use of the apparatus. The turntable and central region of the frame are preferably calibrated to enable a required angle of abduction to be selected for insertion of an implant cup by rotation of the turntable portion about said at least one axis.

The light-source may be mounted on a faceplate portion and said faceplate portion may be fixed to said turntable portion to extend substantially at right angles from said turntable portion in a plane substantially parallel to said at least one axis of pivoting. This faceplate portion may however also be pivotable relative to the turntable about an axis perpendicular to said at least one axis, thereby enabling variation of the angle of anteversion or retroversion, as required. In this variant of the invention, the faceplate portion may therefore be displaced into dispositions in which it is not parallel to said at least one substantially perpendicular axis. Preferably calibration means are provided for indicating the relative angular disposition of the faceplate with respect tot he turntable.

A preferred angle of abduction is 45° and a zero angle of anteversion/retroversion is favoured for many applications. The turntable portion is therefore rotated so that the light beam extends from the light-source at a 45 angle of abduction, i.e. generally at 45° relative to the spinal direction of a patient's body. The reflector or mirror is mounted on the implant insertion means in such a way that when the incident reference beam is reflected back on itself by the reflector, the plane of the flat face of the acetabular cup is in the desired orientation with respect to the anatomical reference plane. It therefore then occupies a plane perpendicular to the beam of light.

For use under surgical conditions, the various components of at least the frame of the apparatus of the invention are preferably formed from material capable of ready sterilisation such as stainless steel. It may also be a disposable unit, the frame being formed from, for example, a plastics material, and discarded after one use.

The invention also provides a method for facilitating aligned location of an acetabular implant in hip joint replacement comprising the steps of defining a reference plane by locational juxtaposition of frame means adjacent selected pelvic features of the patient, and determining the disposition of an implant positioning means with respect to said reference plane so that the disposition of an implant received on an implant mounting portion of said positioning means relative to said reference plane may be monitored, controlled and aligned, for correct placement of the implant in the socket of the acetabular.

In a further aspect, the present invention also provides training apparatus for placement of an acetabular implant in hip joint replacement, comprising pelvic simulation means having a plurality of features together defining a reference plane, frame means for locational juxtaposition adjacent to said features, and means for determining the disposition of an implant positioning means with respect to said reference plane so that the disposition of an implant received on a mounting portion of said implant positioning means relative to said reference plane may be monitored and controlled. In a preferred embodiment of this aspect of the invention, said reference plane defining means comprises portions corresponding to the anterior superior iliac spines of the pelvis and at least one further portion corresponding to the pubic tubercles of the pelvis.

Thus the invention provides a system for placing an acetabular cup in total hip arthroplasty at a desired orientation, this orientation being defined with respect to a fixed anatomical reference plane. This plane is preferably defined by the hereinabove recited anatomical points of the pelvis. These features lie in a single coronal plane. The reference beam used in the preferred embodiments of the invention may be any collimated beam, such as a collimated beam of electromagnetic radiation capable of visual detection or detection by other means. The reflector may be any surface capable of reflecting the reference beam, such as a mirror. The orientation of the acetabular cup may be defined by the orientation in space of the plane of the face of the acetabular cup, the curved face of the cup being received within the socket. The frame means or reference frame is attached to or associated with the anatomical features mentioned previously. The implant positioning means or inserter is used by the surgeon to place the acetabular cup in the appropriate cavity in the pelvis.

The beam source is associated with or attached to the reference frame, after this has been attached to or associated with the anatomical features, in such a way that the direction of the collimated reference beam emitted by this source is known with respect to the anatomical features. A reflector is attached to the inserter in such a way that the trigometrical relationship between it and the plane of the face of the acetabular cup is known or defined. The direction of the reference beam relative to the anatomical reference plane and the relationship between the reflector and the plane of the face of the acetabular cup are selected so that when the incident reference beam is reflected, for example, back on itself by the reflector, the plane of the face of the acetabular cup is int he desired orientation with respect to the anatomical reference plane.

Thus the present invention has an adjustable frame which is placed over the abdomen of the patient and is firmly located on the four promontories of the pelvis noted above. The frame acts as a reliable and constant reference plane. The frame carries the source of a narrow beam of electromagnetic radiation, which may be, but is not necessarily, a source of laser emission, and this is directed at a predetermined angle towards a reflector attached to the shaft of a socket holder. The reflector is oriented relative to the shaft of the holder, and the socket, when mounted on the holder, is also aligned, in each case in such a manner that when the reflected beam strikes a target which is located on the reference plane, an which may itself also be the source of the beam, the socket is correctly aligned. The apparatus is arranged so that the position at which the reflected beam strikes the target is visible to the surgeon and is sensitive to the angularity of the socket holding device. The combined effect of the beam, the reflector and the target magnifies angular movement of the socket holder, to enable the surgeon to position the socket consistently to an accuracy within 1° of the optimum angle for cementing the socket into the acetabular. This accuracy represents a considerable improvement on the accuracy usually achievable in the absence of the guidance provided by the present invention.

Accordingly, the apparatus and method of the invention facilitate accurate insertion of acetabular sockets into acetabular cavities, which operation is an essential part of total hip joint replacement. The invention provides a reliable datum plane from which the optimum angle of insertion of the socket may be established. The invention provides a guide facility enabling the surgeon to orient the socket within the prepared acetabular cavity to a greater accuracy and with greater consistency than any other apparatus presently available.

In its training aspect, the invention provides means enabling a surgeon to improve and perfect his implant positioning technique. For this purpose, the implant is aligned and inserted into a receiving portion of a simulated pelvis, which may be either a simplified model of the pelvic structure or an exact reproduction of the pelvic bones. During such training exercises, the entirety of the pelvic model may be draped, so that the surgeon then has to work without a view of the implant site, as is the case in the operating theatre.

The term mirror as used herein in the foregoing definitions of the invention may be regarded as being equivalent to any other form of reflector means, capable of redirecting an impinging electromagnetic beam, such as a light beam. The frame means of the invention is preferably adjustable, so that the relative dispositions of the wing portions and said further portions may be varied to accommodate different dimensions of the pelvic bone structure. The apparatus of the invention may therefore be used for patients of varying sizes and ages.

BRIEF DESCRIPTION OF THE DRAWINGS

The invention will now be further described having regard to the accompanying drawings, of which.

DETAILED DESCRIPTION OF THE DRAWINGS

Figure 1:
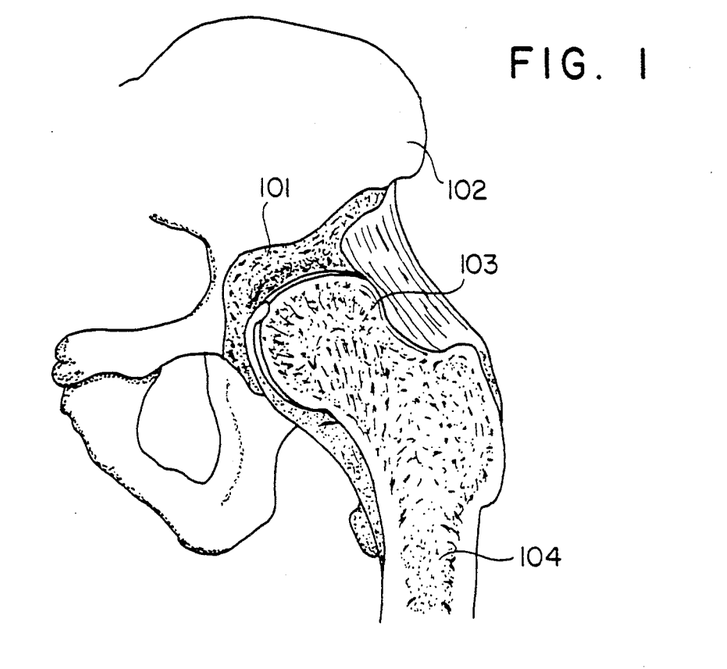
FIG. 1 is a view of a normal hip joint.
Figure 2:
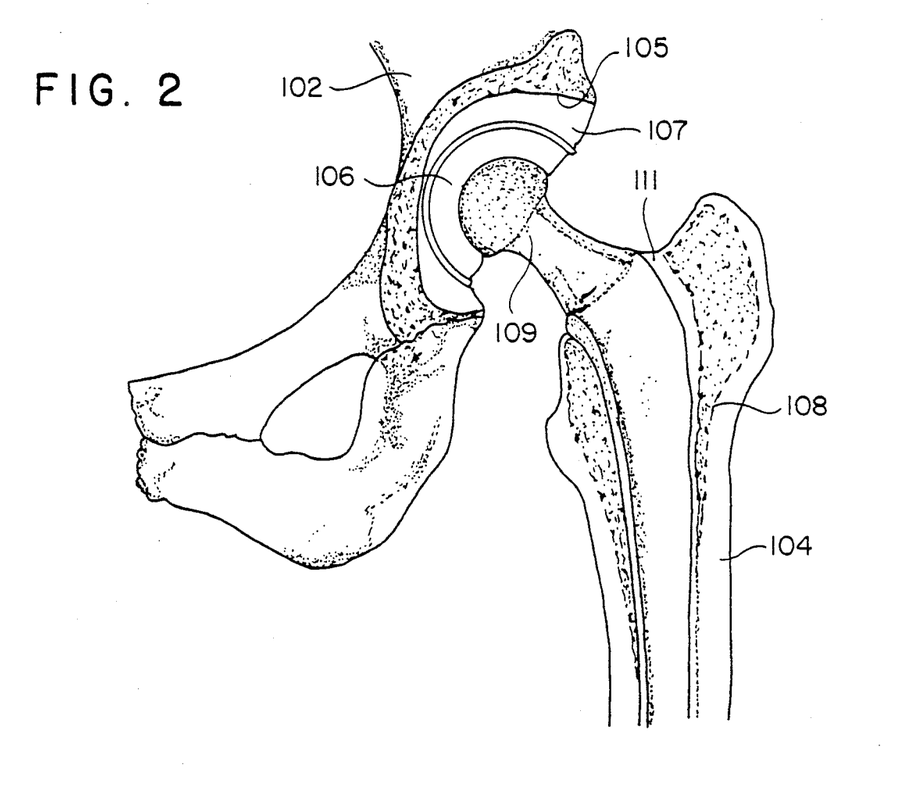
FIG. 2 is a view of a total hip replacement.

A normal human hip joint is shown in FIG. 1 and a totally replaced hip is shown in FIG. 2. As shown in FIG. 1, the hip joint has a socket 101 in the pelvic bone structure 102. A ball head 103 at the upper end of upper leg bone 104 is received in socket 101, in the normal healthy condition.

Figure 3:
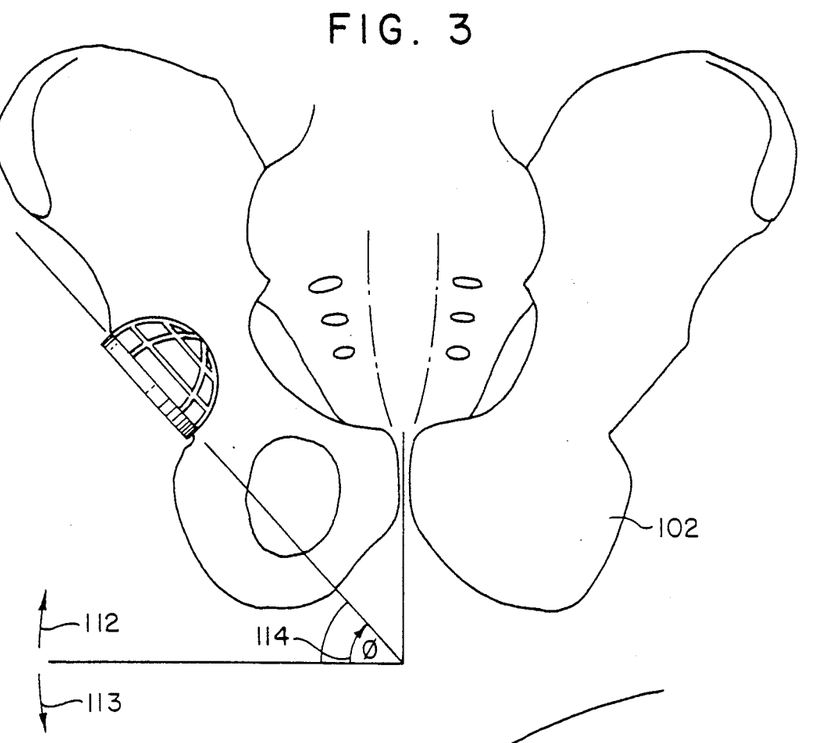
FIG. 3 is a front view of the pelvic bone showing the location of an acetabular socket.
Figure 4:
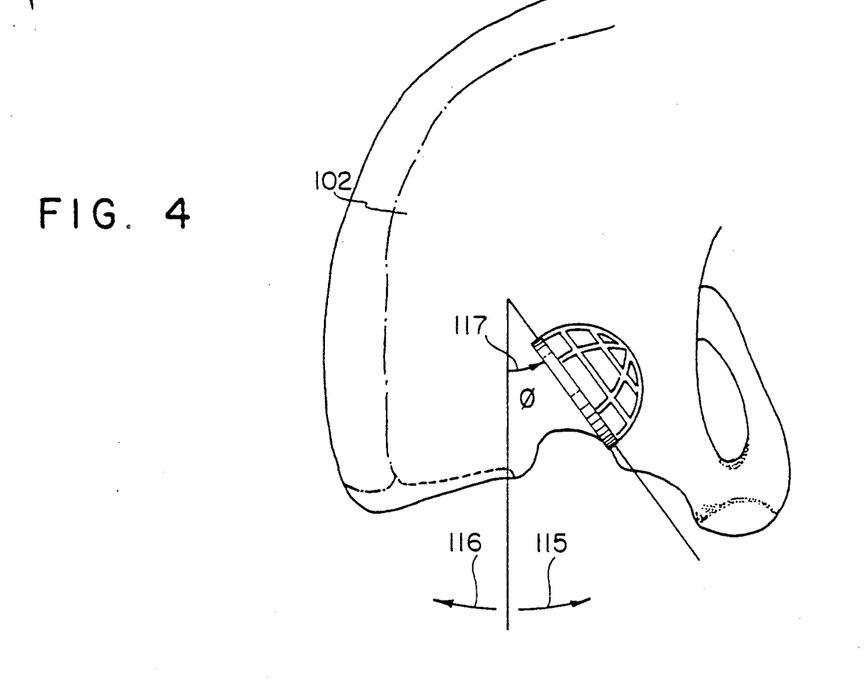
FIG. 4 is a top view of one side of the pelvis, showing the location of an acetabular socket.

As can be seen from FIG. 2, in total hip joint replacement the socket 101 of the hip bone structure 102 is reamed out, indicated by reference 105, and an acetabular cup 106 is cemented in position within the reamed out region 105, the cement being designated by reference 107. The head 103 of bone 104 is also removed, bone 104 is opened out by drilling, indicated at reference 108, and a ball and socket 109 are inserted into this opened-out bone 104, again held by cement, reference 111. The replacement acetabular component 106 faces mainly outwardly and downwardly. The precise orientation of the acetabular component is defined in terms of angles of abduction, adduction, anteversion, and retroversion, which are indicated in FIGS. 3 and 4, these being a front view and a right hand side view of the pelvic bone structure 102. In FIG. 3, the direction of abduction is designated by reference 112 and the direction of adduction by reference 113. Reference 114 indicates an angle of abduction. In general the alignment property in question corresponds to a sidewise pivoting of the insert within the socket cup 106. In FIG. 4, the direction of anteversion is designated by reference 115 and that of retroversion by reference 116. Reference 117 designates an angle of anteversion. Anteversion generally corresponds to tilting of the insert within the socket cup 106 in a vertical direction. A zero angle of anteversion is favoured in many instances.

Figure 5:
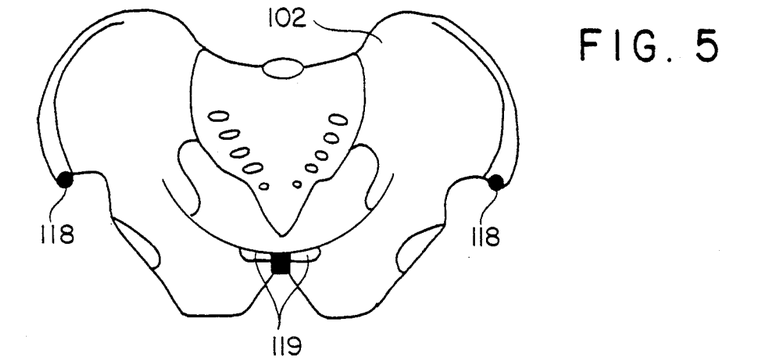
FIG. 5 is a front view of the pelvic bone structure showing the features with which the frame of the apparatus of the invention co-operates.
Figure 6:
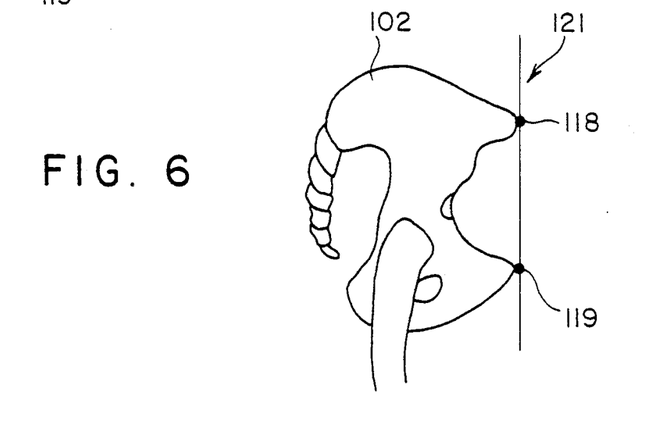
FIG. 6 is a side view of the pelvic bone structure, indicating the vertical plane defined by the features identified in FIG. 5.

Referring now to FIGS. 5 and 6, reference points are required which have a fixed relation with the acetabulum and which can be readily identified during a hip operation, for correctly orienting the angles of abduction and anteversion during the operation. The two anterior superior iliac spines 118 and the two pubic tubercles 119 lie in a single substantially vertical plane 121 when the body is in a standing disposition, as shown in FIG. 6. These points provide an excellent reference base for use in orienting the acetabular cup in a hip joint replacement operation. The relationship between a plane defined by these points and the required plane of orientation is a relatively simple one. In addition, these features of the pelvic structure can easily be felt through the skin, which makes them readily identifiable by the surgeon.

Figure 7:
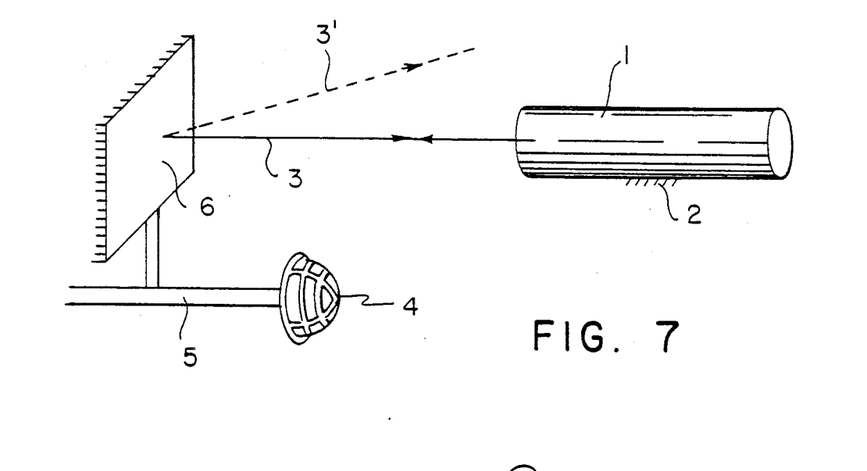
FIG. 7 is a schematic diagram showing the principle of operation of the invention.

Accordingly, the invention uses a referencing frame which is associated with the aforementioned reference points to give a platform on which equipment can be mounted for orienting the acetabular cup during the operation. The design concept revolves around the fact that any family of parallel planes can be defined by a line normal to those planes. Accordingly, having regard now to the schematic diagram of FIG. 7, a laser light source 1 is fixed to the reference frame 2, which is associated with the pelvic features, and a beam 3 of laser light is launched form this source in such a direction that it is normal to a desired orientation plane of the planar face of the acetabular cup 4. A refection device is then mounted on the insertion device 5, in the form of a mirror 6, which lies in a plane parallel to the plane of the acetabular cup planar face. Accordingly, when the beam of light is reflected back on itself, i.e. the incident and reflected beams lies along the same line, the mirror must then be in the correct plane, which in turn implies that the acetabular cup is also in the correct plane, so that it is properly aligned for reception in the cavity of the pelvic bone structure. If the incident and reflected beams do not lie along the same path, such as is the case when the reflected beam follows the path 3' designated in dotted line in FIG. 7, then this indicates that the alignment of the acetabular cup is incorrect and further adjustment is required preparatory to final implantation.

Figure 8:
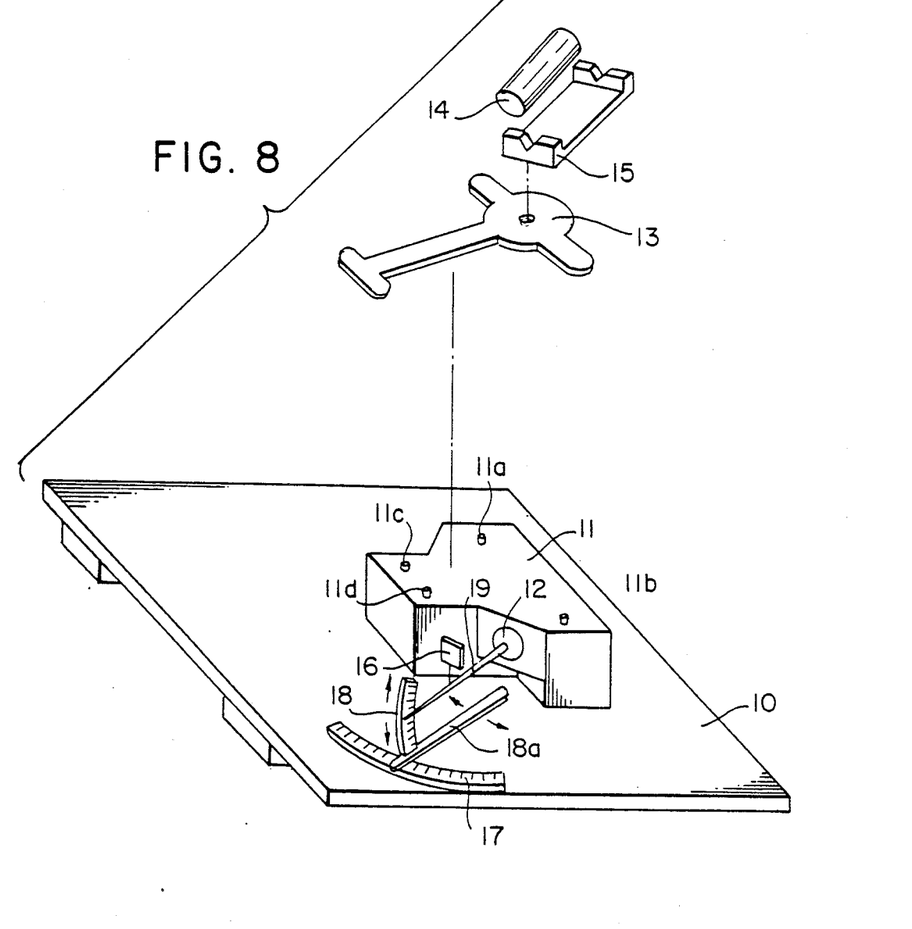
FIG. 8 is a pictorial representation of an experimental apparatus demonstrating the principle of operation of the invention.

FIG. 8 is a pictorial view of apparatus for testing the method of the invention. As shown in FIG. 8, the apparatus comprises a pelvis simulation block 11 mounted on a baseboard 10, which is a simple imitation of the pelvis, and has frame-receiving reference points 11a, 11b, 11c, 11d and acetabular sockets 12 in their correct relative positions. A test mounting frame 13 is provided on which the laser source 14 is mounted by one or other of various methods or means 15. The laser source may be a HeNe device, for directing a beam towards the mirror 16 of the test apparatus. Orientation monitoring equipment of the apparatus consists of two orthogonally-mounted angle scales 17, 18, as shown on the drawing, for identifying the orientation at any given time, and serves to assess the sensitivity of the system. The mirror is mounted on a swivel-jointed arm 19, for simulating the way in which the acetabular cup can be moved about in the cement during insertion, in an actual surgical operation. The lateral angular scale 17 is fixed to baseboard 10. The vertical scale 18 is mounted at the free end of a pivoting arm 18a, pivotably mounted on baseboard 10, so that the vertical scale may also traverse with sidewise displacement of the mirror-carrying arm 19. Movement of arm 19 about its pivotable connection 12 to simulation block 11 enables the change in the direction of the reflected light beam to be observed for specific and measurable angular orientations of arm 19 and therefore also for the angular disposition of a notional acetabular cup in a pelvis.

The test apparatus of FIG. 8 may also serve as a training device. For this, the pelvis simulation block 11 is draped and the surgeon is then required to position an implant in socket 12 using the alignment system of the invention. The surgeon may also compare his performance using the system of the invention with the results when working blind, that is, using feel and experience only. Experimental figures for the accuracy of placement of inserts using the system of the invention suggest that most users will place the inserts more precisely and consistently when making use of the invention than when working without an alignment aid. In its adaptation as a training device, the apparatus of FIG. 8 may have arm 19 and scales 17 and 18 removed, the trainee using a cup insertion device of a practical kind to apply an acetabular cup to the simulated socket at location 12. Alternatively however, the apparatus may be used exactly as shown in the drawing, for a user to develop a feel for the sensitivity of the apparatus against measured angular deviations from a desired placement orientation for the cup.

Figure 9:
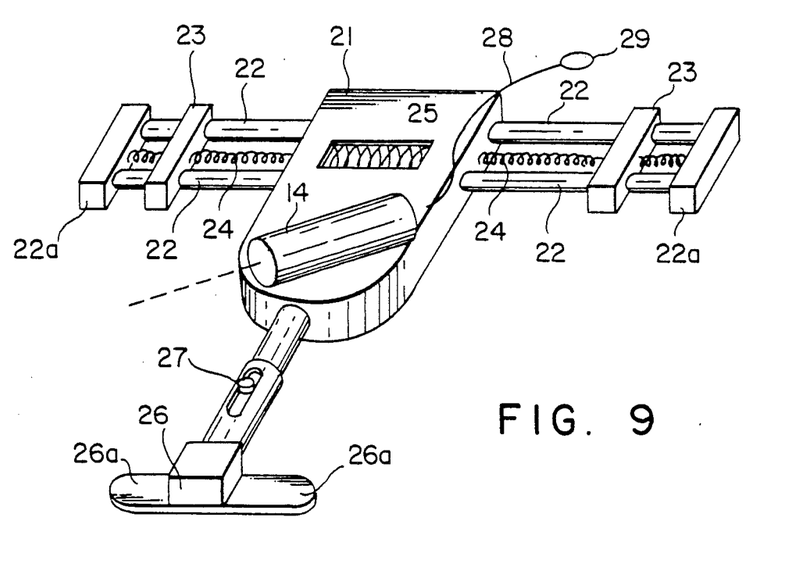
FIG. 9 is a pictorial view of an adjustable variant of the frame of the apparatus.

The practical embodiment of apparatus frame according to the invention shown in FIG. 9 has a central block 21 from which there extend lateral guide members 22 terminating at fixed end blocks 22a carrying wing portions 23 for alignment with the anterior superior iliac spines. A screw mechanism 24 operated manually by a knurled cylinder 25 allows inward and outward adjustment of the dispositions of the wing portions 23, so that they may be correctly set in position for any size of pelvic bone structure. The portions 26a, 26b of the frame which align with the pubic tubercles are on a block 26, which is similarly telescopically adjustable in position relative to the central mounting portion 21 of the frame, and may be locked in position by a screw and lock-nut device 27. Light source 14 is mounted on control block 11 and connected to an external power point by cable 28 and plug 29.

The apparatus may alternatively incorporate a fibre optic cable to bring the laser or other light beam from the source to the frame. This facilitates a compact construction, as an actual laser source may be larger than would be desirable for mounting on the frame. An associated optical lens system is then required. The apparatus may also be associated with electronic circuitry for giving a visual and/or audio indication when correct alignment is achieved. Photodiodes either singly mounted or in an array may be used. The method may require a somewhat different configuration of mounting device from that currently used by surgeons. In addition, the mounting arrangement may be constructed so that different orientations of the acetabular cup may be accommodated.

In use of the method of the invention, whether on a patient using the frame of FIG. 9 or for experimental purposes using the test apparatus of FIG. 8, the laser is switched on, the acetabular cup in mounted on the end of the mounting member or alternatively the test rod is displaced, and this adjustment or displacement continues until the beam reflected by the mirror mounted on the mounting member or on the experimental swivel-rod, as the case may be, lies in line with the incident beam of light emitted by the laser. The orientation of the planar face of the acetabular cup is then correct. In order to achieve this, the laser source is mounted on the frame and the mirror is mounted on the arm or the mounting member in such a way that when this coincidence of the emitted and reflected beams takes place, acetabular cup alignment is correct.

Figure 10A:
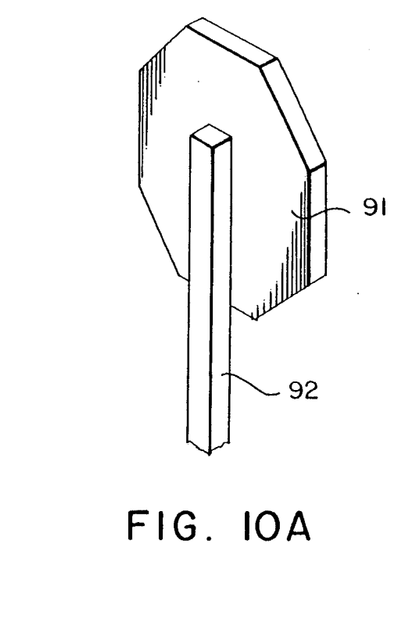
FIG. 10A is a pictorial view of a mirror and mirror support for use with the apparatus of FIG. 10B.

An especially favoured practical embodiment of apparatus according to the invention will now be described, having regard to FIGS. 10, 11 and 12.

Figure 10B:
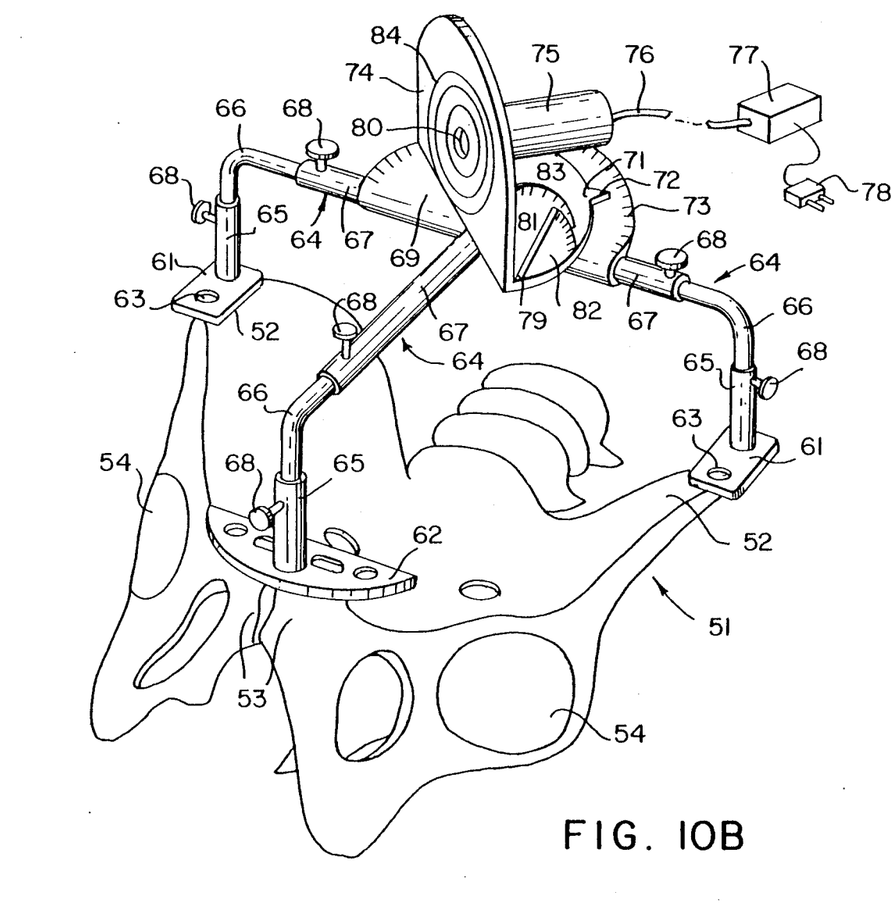
FIG. 10B is a pictorial view of a favoured construction of apparatus according to the invention applied to a pelvic structure.

As shown in FIG. 10, a pelvic bone structure 51 has anterior superior iliac spines 52 and pubic tubercles 53.

Socket locations for reception of acetabular cups are designated by reference 54. The anterior superior iliac spines and the two pubic tubercles lie in the same vertical plane in the standing position, this being referred to as the coronal plane. These readily identifiable anatomical features provide ideal reference points for accurate monitoring of body position during an operation for hip join repair. The position of the anterior superior iliac spines is conventionally one of the main landmarks used to position the acetabular cup. However, this positioning has previously depended on clinical judgement, and pelvic rotation under the drapes can lead to cup misalignment.

Using the four anatomical reference points previously mentioned, a reference system can be set up with respect to the angles of anteversion/retroversion and abduction of the acetabulum which is independent of body position. A frame structure suitable for this purpose is shown in FIG. 10. Rear feet 61 of the frame are attached to the anterior superior iliac spines and a front foot 62 is attached to the pubic tubercles. Each foot has fixing apertures 63, for the passage of sharp pins by means of which the feet are secured to the reference pints. Limbs 64 extend from the feet 61 and 62 to a central region of the frame structure. Each limb is made up of a foot socket portion 65, an angle connector 66 and a tubular limb portion 67 extending outwardly from the central region of the frame. Locking devices 68, which may be in the form of set screws, hold the various limb portions together. The central region of the frame is defined by a baseplate 69.

A turntable 71 is mounted on the baseplate 69 for rotational displacement about a generally vertical axis, in the disposition of the apparatus shown in FIG. 10. A pointer 72 on the turntable 71 enables the angular disposition of the turntable relative to the baseplate to be determined, basepalte 71 carrying suitable insignia 73 indicating the angular relativity of the baseplate and turntable 71 in cooperation with pointer 72. This rotational movement of the turntable determines the angle of adduction or abduction to be used in placement of an implant in the socket 54. The angle of adduction or abduction can be generally regarded as sidewise rotation of the implant within the socket about a generally vertical axis in the depiction of FIG. 10.

The turntable 71 carries a faceplate 74 which in turn carries a mount 75 for the light-source. This light-source may be any device for directing a collimated beam through aperture 80 in the faceplate 74. The collimated light beam is preferably established by a terminating device, suitably incorporating a lens system, on an optic fibre 76 extending from the mount 74 to a light generator 77. Generator 77 may be fed by a conventional electrical supply connector, designated by reference 78.

As shown in FIG. 10, the faceplate 74 is pivotably mounted relative to turntable 71 by means of a hinge 79. In this way the faceplate may be tilted forwardly and rearwardly relative to the turntable about an axis defined by hinge 79 which is substantially at right angles to the axis of rotation of the turntable. The axis of hinging displacement of the faceplate is thus generally parallel to the coronal plane defined by the anatomical reference points. Tilting of the faceplate in this way corresponds to anteversion or retroversion of the implant in the socket 54, which may be generally described in terms of forward and rearward displacement of the top and bottom of the implant about a generally horizontal axis in the representation of FIG. 10. Co-operating sectors 81 on faceplate 74 and 82 on turntable 71 enable selection of a required degree of ante- or retroversion, depending on the relative positions of calibration marks 83.

Figure 11:
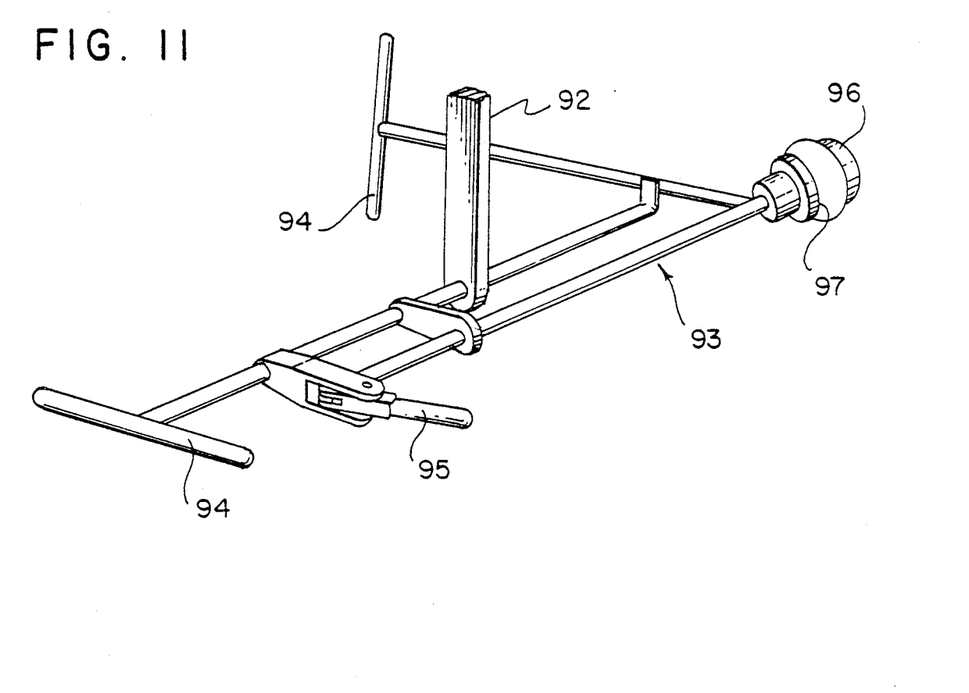
FIG. 11 is a pictorial view of an implant insertion device with which the present invention may be used.

In use of the apparatus, the light beam is directed through the aperture 80 towards a mirror 91, mounted at the upper end of a mirror support 82, the lower end of which is attached to a socket support and insertion device 93, shown in pictorial view in FIG. 11. The mirror 91 is mounted on device 93 in such a manner that the plane of the mirror is parallel to the plane of the flat face of the insert 96 received at the front end 97 of the device. The insert unit has two handles 94 arranged to extend at right angles to each other, for use by the surgeon in placement of an insert cup 96. A socket release mechanism 95 is operable to disengage the insert 96 from the device following placement in a socket 54.

Figure 12:
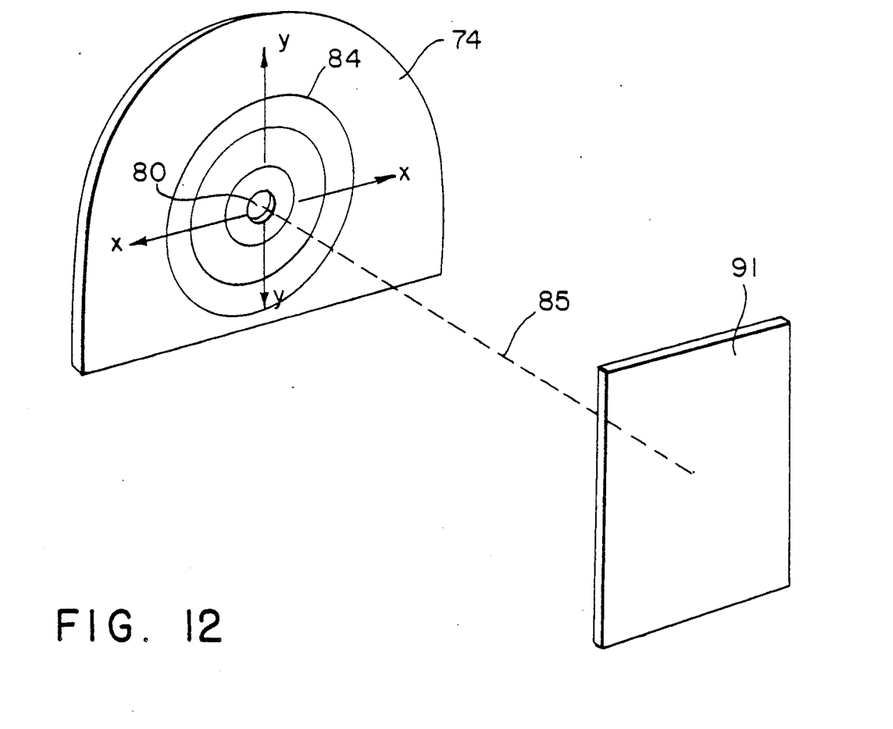
FIG. 12 is a schematic representation of the use of reflected light by the system of the invention to indicate the angular disposition of an acetabular cup undergoing insertion.

The functioning of the invention is shown in schematic form in FIG. 12. In summary, the frame of the invention is attached to the four anatomical body reference points and a collimated beam of light is emitted from the source mounted on the reference frame, arranged to point in a direction normal to the desired plane of orientation, and the reflector attached to the cup insertion device parallel to the lane of the acetabular cup is used to achieve accurate orientation of the cup by reflecting the beam back on itself. The system thus is independent of differences in pelvic dimensions and is essentially based on the concept that any family of parallel planes can be defined by a line normal to those planes. As shown in FIG. 12, the collimated beam of light 85 is launched form the reference frame in such a direction that it is normal to the desired orientation plane of the acetabular cup. Reflection of this beam back from the mirror mounted on the cup insertion device, parallel to the planar face of the cup, back on itself, i.e. when the incident and reflected beam lie along the same line, shows that the cup is in the correct disposition. In use of the invention, the surgeon therefore adjusts the disposition of the insertion device until such time as this coincidence of the emitted and reflected beams is achieved. To facilitate the surgeon in this task, the faceplate 74 is provided with target markings of generally bullseye form, as designated by reference 84.

The angular calibrations 73 for adduction and abduction and 83 for anteversion and retroversion are established during production of the apparatus or on a simulation device. In use of the invention, the frame portion of the apparatus is first fixed symmetrically on the four bony points of the body. The beam source is then adjusted to the desired cup position on the mounting, i.e. to the required angle of abduction and/or anteversion or retroversion as required. In the representation of FIG. 12, angular displacement of the reflected beam along the horizontal or X axis corresponds to variation in angle of abduction, while displacement along the vertical or Y axis represents anteversion or retroversion. For many uses, the angle of anteversion/retroversion is selected as zero and the angle of abduction is preferably 45°. The reflection of the beam back on itself from the reflector allows the cup position to be determined. The surgeon manipulates the inserter to which the mirror is affixed until such time as this coincidence of incident and reflected beams occurs, at which time the insert may be detached and placement proceed in the normal manner.

The surgical procedures in question require draping of the area to be dealt with, exposing of the upper femur, further procedures to give access to the hip as required, cleaning and preparation of the acetabulum, and the boring of drill holes to anchor cement. Following placement of cement, the cup is introduced and oriented using the means of the invention. Experiments have shown that sue of the device and system of the invention, while adding a small amount of time to the operative procedure, ensures accurate cup analysis and improves the range of alignment in both the anteversion/retroversion and abduction directions by a figure in excess of three hundred percent compared with conventional previous techniques. The device of the invention is therefore suitable for two specific applications, first of all primary arthroplasty and secondly in revision surgery, where especially precise positioning is required.

The device of the invention enables such precise positioning with predeterminable selection of the angles of abduction and anteversion/retroversion being possible as required for any individual patient.

The apparatus of FIG. 10 may also be deployed as a training system, the pelvic structure 51 representing an exact model of the pelvic bone structure. As before, this part of the training system is draped and the surgeon then attempts to plant the implant in a cup 54 using the guidance system provided by the light and reflector arrangement. Again, the surgeon may compare performance with and without the guidance provided by the invention.

In summary therefore, the invention provides a novel guidance system for use in hip joint replacement, which serves both to improve the accuracy and consistency of acetabular cup implantation in surgical use and also enables surgeons to improve their operating technique in a training environment, using simulation apparatus incorporating the principles of the invention.

We claim:

1. Apparatus for facilitating aligned location of an acetabular implant in hip joint replacement, comprising frame means adapted to bear against a plurality of protrusions of a pelvis of a patient to define a reference plane, said frame means having means to display the position of said reference plane, implant positioning means having means for holding a said implant, and means for determining the disposition of said implant positioning means with respect to said reference plane so that the disposition of an implant on said holding means relative to said reference plane may be monitored and controlled.

2. Apparatus according to claim 1, comprising means for affixing said frame means to said protrusions of said pelvis.

3. Apparatus according to claim 1, wherein the frame means has wing portions for juxtaposition adjacent the anterior superior iliac spines of the pelvis and a further portion for juxtaposition against the pubic tubercles of the pelvis.

4. Apparatus according to claim 1, wherein said means for determining the disposition of the implant positioning means includes means for emitting a directed beam and target means towards which said beam is directable, correct alignment of the implant positioning means being indicated by impact of the beam on a specified region of the target means.

5. Apparatus according to claim 4, wherein said means for determining the disposition of the implant positioning means includes a reflector mountable on the implant positioning means to reflect said directed beam towards said target means.

6. Apparatus according to claim 4, wherein said means for determining the disposition of the implant positioning means comprises a light source mounted on the frame means for reflection of said beam back along its initial path when the implant positioning means is correctly aligned.

7. Apparatus according to claim 1, wherein the frame means comprises two foot portions that bear against anterior superior iliac spines of the pelvis and at least one further foot portion that bears against at least one pubic tubercle of the pelvis, a central frame region from which limbs extend to said foot portions, and a light-source mounting portion which is pivotably displaceable relative to said central region of the frame about said at least one axis.

8. Apparatus according to claim 7, wherein the frame is so dimensioned that when said foot portions bear against said iliac spies and pubic tubercles, said at least one axis extends substantially perpendicular to a plane in which the farthermost protruding portions of said iliac spines and pubic tubercles are contained.

9. Apparatus according to claim 7, wherein the spacing of said foot portions from said central region of the frame is adjustable to enable use of the apparatus of the invention on a variety of different sizes of patient and under a diversity of operating conditions.

10. Apparatus according to claim 7, and means for changing the orientation of the foot portions relative to the central region of the frame.

11. Apparatus according to claim 7, wherein the light-source mounting portion of the frame has means for receiving a source of collimated light for direction towards a reflector mounted on said implant positioning means, said reflector defining a further portion of the means for determining the disposition of the implant positioning means.

12. Apparatus according to claim 11, wherein the light-source mounting means comprises a turntable portion which is rotatable relative to said central region of the frame about said at least one axis.

13. Apparatus according to claim 12, wherein the light-source is mountable for direction of a light beam substantially at right angles to said at least one axis.

14. Apparatus according to claim 12, the turntable and the central region of the frame having calibrations thereon to enable a required angle of abduction to be selected for insertion of an implant cup by rotation of the turntable portion about said at least one axis.

15. Apparatus according to claim 12, wherein the light-source is mounted on a faceplate portion and said faceplate portion is fixed to said turntable portion to extend substantially at right angles from said turntable portion in a plane substantially parallel to said at least one axis.

16. Apparatus according to claim 12, wherein the light-source is mounted on a faceplate portion, and means mounting said faceplate portion for pivoting movement relative to the turntable about an axis perpendicular to said at least one axis, thereby enabling a required angle of anteversion or retroversion to be selected for insertion of an implant cup.

17. Apparatus for facilitating aligned location of an acetabular implant in hip joint replacement, comprising frame means adapted to bear against a plurality of protrusions of a pelvis of a patient to define a reference plane, said frame means having means to display the position of said reference plane, implant positioning means having means for holding a said implant and for positioning a said implant in a hip socket, and means for determining the disposition of said implant positioning means with respect to said reference plane so that the disposition of an implant on said holding means relative to said reference plane may be monitored and controlled.

18. Apparatus for facilitating aligned location of an acetabular implant in hip joint replacement, comprising utilizing frame means adapted to bear against a plurality of protrusions of a pelvis of a patient to define a reference plane, said frame means having means to display the position of said reference plane and implant positioning means having means for holding a said implant, and determining the disposition of said implant positioning means with respect to said reference plane so that the disposition of an implant on said holding means relative to said reference plane may be monitored and controlled.

19. Training apparatus for training in the aligned location of an acetabular implant in hip joint replacement, comprising frame means adapted to bear against a simulation of a plurality of protrusions of a pelvis of a patient to define a reference plane, said frame means having means to display the position of said reference plane, implant positioning means having means for holding a said implant, and means for determining the disposition of said implant positioning means with respect to said reference plane so that the disposition of an implant on said holding means relative to said reference plane may be monitored and controlled.

20. Training apparatus according to claim 19 wherein said protrusions comprise simulations of anterior superior iliac spines of the pelvis and at least one pubic tubercle of the pelvis.

* * * * *